United States Patent [19]

Schaeffer

[11] 4,060,616
[45] Nov. 29, 1977

[54] PURINE DERIVATIVES WITH REPEATING UNIT

[75] Inventor: Howard John Schaeffer, Richmond, Va.

[73] Assignee: Burroughs Wellcome Co., Research Triangle Park, N.C.

[21] Appl. No.: 662,899

[22] Filed: Mar. 1, 1976

[51] Int. Cl.$^2$ .................... A61K 31/52; C07D 473/16; C07D 473/18; C07D 473/32

[52] U.S. Cl. .................................... 424/253; 260/252; 260/254

[58] Field of Search ................. 260/254, 252; 424/253

[56] References Cited

PUBLICATIONS

Schaeffer, J. Med. Chem., vol. 14 (1971), pp. 367-369.

Primary Examiner—Paul M. Coughlan, Jr.
Attorney, Agent, or Firm—Donald Brown

[57] ABSTRACT

9-[2-(2-Hydroxyethoxy)ethoxymethyl] and related derivatives of certain 2-amino-6-substituted purines have been discovered to have potent anti-viral activities. Novel compounds and their pharmaceutically acceptable salts, pharmaceutical formulations containing the compounds of this invention, and the treatment of viral infection with these formulations are all disclosed. 9-[2-(2-hydroxyethoxy)ethoxymethyl] guanine and 2-amino-9-[2-(2-hydroxyethoxy)ethoxymethyl] adenine, i.e. 2,6-diamino-9-[2-(2-hydroxyethoxy)ethoxymethyl] purine, are examples of especially active compounds of this invention.

87 Claims, No Drawings

PURINE DERIVATIVES WITH REPEATING UNIT

This invention relates to purine compounds with repeating groups and their pharmaceutically acceptable salts and to methods of preparing them.

It has now been discovered that substituted purines of formula (I)

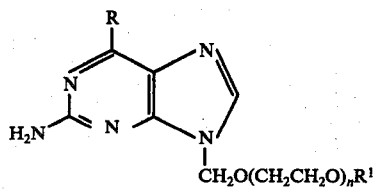

wherein R is halogen, preferably chlorine or bromine, hydroxy or amino; $R^1$ is hydrogen or $R^1$ is

where $R^2$ is hydrogen, straight or branched alkyl containing 1 to 8 preferably 1 to 4 carbon atoms or aromatic containing 6 or 10 carbon atoms, i.e. phenyl or naphthyl; and $n$ is an integer from 2 to 10, preferably 2 to 4 and most preferably 2, have antiviral activity against various classes of DNA and RNA in vitro. In particular, the compounds are especially active against influenza, vaccinia, and herpes viruses, including simplex, zoster and varicella, in mammals, which cause such diseases as for example herpetic keratitis in rabbits and herpetic encephalitis in mice.

According to the present invention there is provided a compound of formula (I), as defined above or a salt thereof, especially in the form of a pharamaceutically acceptable salt.

A compound of formula (I) wherein R is hydroxy and $R^1$ is hydroxy or a salt thereof, is preferred.

Salts which are especially convenient for therapeutic use are salts of pharmaceutically acceptable organic acids such as lactic, acetic, malic, or p-toluenesulphonic acid as well as salts of pharmaceutically acceptable mineral acids such as hydrochloric or sulphuric acid. Other salts may also be prepared and then converted by conventional double decomposition methods into salts directly suitable for purposes of treatment of viral infections in mammals.

In a second aspect of the present invention there is provided a method of preparing a substituted compound of formula (I) as hereinbefore defined, characterised in that:

a. a compound of formula (II), wherein M and G are precursors of an hydroxy and amino group respectively, is converted

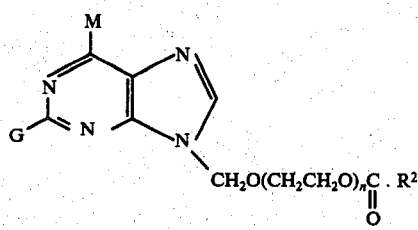

into a compound of formula (I);

b. a compound of formula (III)

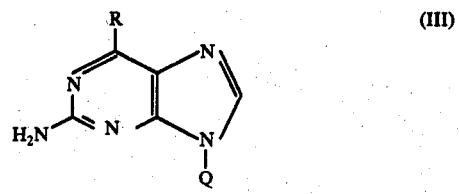

is reacted with a compound of formula (IV)

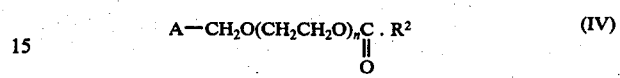

wherein A is a leaving atom or group and Q is a hydrogen atom or a leaving group;

c. a ring is closed in a precursor compound having either the pyrimidine, or imidazole ring incompletely formed;

d. The alcohol corresponding to a compound of formula (I) is esterified by reaction with formic acid;

e. a blocking group is removed from a compound of formula (I) wherein one or both of the hydroxy and amino groups is blocked; and where the product of said reaction is a base optionally converting a compound of formula (I) into an acid addition salt or alkali metal salt thereof, or where the product is a salt of a compound of formula (I), optionally converting said salt into its base or another salt thereof.

Conversion of a compound of formula (II), by method a), can be achieved in numerous different ways. For example M can be converted into hydroxy by hydrolysis, and G and or M can be be converted into amino by aminolysis. All such methods are well known and can be found in "Heterocyclic compounds — Fused Pyrimidines Part II Purines ed. by D. J. Brown (1971) published Wiley-Interscience".

Alternatively conversion can be brought about by using enzymes, for example adenosine deaminase efficiently converts a 2,6 diamino compound into the required guanine, in an aqueous suspension at about 37° C and initial pH of about 7.0.

Those compounds that contain precursors of the hydroxy and amino groups, and can be converted into compounds of formula (I), can be considered as intermediates in the synthesis of those compounds.

In method b) the leaving atom or group A is a reactive residue of an organic or inorganic acid, and may therefore by an halogen atom, or carboxylate group, and Q is hydrogen or acyl. The preferred method comprises the condensation of a purine having the desired 2 - and 6- substitution with a formyl blocked 2-haloalkoxy-ethanol for instance 2-formyloxyethoxymethyl chloride, in a strong polar solvent such as dimethylformamide (DMF) or hexamethylphosphoramide, and in the presence of a proton acceptor, such as a base e.g. triethylamine or potassium carbonate. The reaction is preferably carried out at room temperature over an extended period of time i.e., several days may be required to give reasonable yields.

Alternatively a thermal condensation, i.e., fusion reaction, may be carried out to give the product directly. For this reaction a suitably sustituted purine is heated together with formyloxyalkoxymethyl carboxylate in the presence of a catalytic amount of a strong acid such as sulphuric acid. Temperatures in excess of 100° C are generally required, but they should preferably not be greater than about 200° C in order to minimise decomposition. The temperature should be selected such that the mixture of reactants fuse i.e., melt, before they undergo decomposition.

The fusion reaction may also be carried under substantially the same conditions as above, with perhaps somewhat lower temperatures, between a 9-acylpurine and and alkoxymethyl carboxylate or halide. Alternatively the fusion reaction can be carried out using the diester for instance 2-formyloxyethomymethyl acetate.

Method c) involves the ring closure of either the imidazole, or pyrimidine ring to give the final product. In the case of the imidazole ring this may be achieved by reaction of the suitably substituted precursor with a one carbon reagent, such a triethyl orthoformate, under for example mildly acidic conditions, at temperature of about 25° C and for several hours. A suitable precursor is a substituted pyrimidine of formula (V)

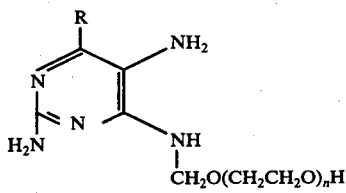

An alternative reagent to use is diethoxymethyl acetate, when neutral conditions at about 100° C for about 10-15 minutes are preferred.

The ring closure of the pyrimidine ring is similar to that for the imidazole ring except that the carbon reagent being added is generally substituted, for example by amino. The blocked, substituted carbon is first attached to the 2-amino group on a precursor of formula (VI)

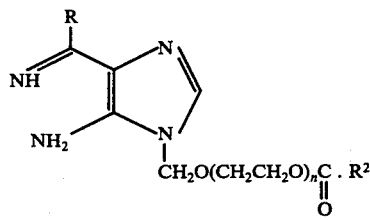

and then deblocked and cyclized. Cyclization may be achieved in some cases by treatment with acid, however this should be done as close to neutral as possible. In other cases a compound of formula (VI) can be closed by reaction with one of the standard one carbon reagents, for example guanidine under mild conditions.

In method d) a compound of formula (VII)

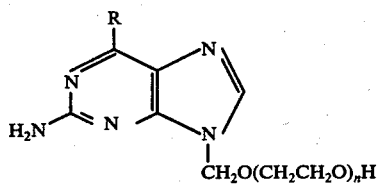

is reacted with formic acid.

In method e) the amino and hydroxy groups may reversibly be blocked by for instance trimethylsilyl groups. Such a compound will be the product of the condensation of a trimethylsilylated purine and an ester or diester. Such blocking groups are very labile and can be removed by solvolysis with alcoholic or aqueous ammonia, or by alcoholysis.

Alternatively the mercuric chloride salt of a purine can be prepared in the presence of alkali and then condensed with a haloether in solvent of the aromatic organic type. Prior to preparation of the salt however all reactive substituents on the purine must be blocked and therefore the last step in this method is the unblocking of the blocked substituents.

In another aspect of the invention there is provided a pharmaceutical composition comprising a compound of formula (I) as hereinbefore defined or a pharmaceutically acceptable salt thereof, together with a pharmaceutically acceptable carrier therefor. In a particular aspect the pharmaceutical composition comprises a compound of formula (I) in effective non toxic unit dose form.

As used herein the term "effective unit dose" is denoted to mean a predetermined antiviral amount sufficient to be effective against the viral organisms in vivo. Pharmaceutically acceptable carriers are materials useful for the purpose of administering the medicament, and may be solid, liquid or gaseous materials, which are otherwise inert and medically acceptable and are compatible with the active ingredients.

These pharmaceutical compositions may be given parenterally, orally, used as a suppository or pessary, applied topically as an ointment, cream, aerosol, powder, or given as eye or nose drops etc., depending on whether the preparation is used to treat internal or external viral infections.

For internal virus infections the compositions are administered orally or parenterally at effective non toxic anti virus dose level, calculated as the free base, of about 0.1 to 250 mg per kg, of mammal body weight, and are used in man in a unit dosage form, administered a few times daily in the amount of 1 to 250 mg per unit dose.

For oral administration, fine powders or granules may contain diluting, dispersing and/or surface active agents, and may be presented in a draught, in water or in a syrup; in capsules or sachets in the dry state or in a non-aqueous solution or suspension, wherein suspending agents may be included; in tablets, wherein binders and lubricants may be included; or in a suspension in water or a syrup. Where desirable or necessary, flavouring, preserving, suspending, thickening or emulsifying agents may be included. Tablets and granules are preferred, and these may be coated.

For parenteral administration or for administration as drops, as for eye infections, the compounds may be presented in aqueous solution in an effective non toxic dose in a concentration of from about 0.1 to 10% more preferably 0.1 to 7%, most preferably 0.2% w/v. The solution may contain antioxidants, buffers, etc.

Alternatively for infections of the eye, or other external tissues e.g. mouth and skin the compositions are preferably applied to the infected part of the body of the patient as a topical ointment or cream in an effective non toxic dose. The compounds may be presented in an ointment, for instance with a water soluble ointment base, or in a cream, for instance with an oil in water cream base, in a concentration of from about 0.1 to 10% preferably 0.1 to 7%, most preferably 1% w/v.

Of the compounds of formula (I) 9-[2-(2-hydroxyethoxy)ethoxymethyl]guanine and 2,6-diamino-9-[2-(2-hydroxyethoxy)ethoxymethyl]purine are most preferred particularly because of their extremely high antiviral activity against Herpes.

In yet a further aspect of the invention there is provided a method of treating viral infections in mammals which comprises the administration of an effective non toxic antiviral amount or dose, as hereinbefore defined, of a compound of formula (I), or a pharmaceutically acceptable salt thereof. Administration is preferably by topical application or by the oral or parenteral route.

The invention will now be illustrated with reference to the following examples.

EXAMPLE 1

2-Amino-6-chloro-9-[2-(2-benzoyloxyethoxy)-ethoxymethyl] purine

Dry HCl gas was bubbled for 4 hours at 0° C. thru a mixture of diethylene glycol monobenzoate (21.8 g) and paraformaldehyde (3.1 g) in dry dichloromethane (180 ml). The reaction mixture was dried over anhydrous calcium chloride and molecular sieves (Linde 3A), filtered and flash evaporated at 45° C. and about 20 mm Hg to give a yellow liquid weighing 26 g. of a mixture of 2-(2-benzoyloxyethoxy)ethoxymethyl chloride and HCl. Distillation of this material gave pure 2-(2-benzoyloxyethoxy)ethoxymethyl chloride as a colorless liquid in substantially quantitative yield, b.p. 143°-145°C/0.25 - 0.3 mm Hg.

A mixture of 2-amino-6-chloropurine (3.0 g) and anhydrous potassium carbonate (2.44 g) in dry dimethylformamide (50 ml) was stirred at room temperature for several hours. To this mixture was added 5 g of 2-(2-benzoyloxyethoxy)ethoxymethyl chloride. The reaction mixture was stirred at room temperature for 4 days and then poured into ice and water. The resulting mixture was extracted with chloroform (3X) and the chloroform extract washed with 10% aqueous acetic acid, with water and then dried over anhydrous sodium sulfate. The solution was filtered and the chloroform evaporated at room temperature and reduced pressure (initially about 20 mm and finally about 1 mm Hg). The residual yellow oil was applied to a column containing silica gel (200 g) in 1:1 ether:chloroform. The column was eluted with 1:1 ether:chloroform followed by chloroform followed by methanol (5%):chloroform (95%). The desired product, 2-amino-6-chloro-9-[2-(2-benzoyloxyethoxy)ethoxymethyl]purine, was eluted in the methanol: chloroform eluate. The fraction exhibiting a single spot on silica gel thin layer chromatography [mobile phase methanol (2%): chloroform (98%)] were combined and evaporated to give a pale yellow oil which gradually solidified. This was recrystallized from benzene to give 2-amino-6-chloro-9-[2-(2-benzoyloxyethoxy)ethoxymethyl]purine 1.5 g), m.p. 111°-112° C.

EXAMPLE 2

2,6-Diamino-9-[2-(2-hydroxyethoxy)ethoxymethyl] purine

A mixture of 2-amino-6-chloro-9-[2-(2-benzoyloxyethoxy)ethoxymethyl] purine (1.2 g) and methanol saturated with ammonia (65 ml) was heated in a bomb at 80° C. overnight. The methanol and excess ammonia was evaporated and the residue partitioned between ether and water. The aqueous solution was evaporated to give a gummy residue which was dissolved in a minimum amount of water and the solution put on a strongly basic ion exchange column (Rexyn 201, 9.0 g). The column was eluted with water; the first 75 ml was collected and evaporated, giving 0.6 g of an oil. This was dissolved in 1:1 methanol:chloroform (40 ml) and silica gel (2 g) added. The solvent was evaporated and the residual mixture transferred to a column of silica gel (20 g) in chloroform. The column was eluted with chloroform (800 ml) and then with methanol (5%):chloroform (95%). Fractions totaling 800 ml of the methanol:chloroform eluate were discarded; the next 1400 ml were collected and evaporated to give 520 mg of an oily residue. This was dissolved in acetone and chilled to give 2,6-diamino-9-[2-(2-hydroxy-ethoxy)ethoxymethyl] purine as off-white needles (250 mg, m.p. 76–82° C.). Elemented analysis indicated that the crystals exist as a partial acetonate. NMR analysis is consistent with the designed structure.

EXAMPLE 3

9-[2-(2-Hydroxyethoxy)ethoxymethyl]guanine

Silver acetate (3.34 g) was added with cooling and stirring to a solution of 2-(2-benzoyloxyethoxy)ethoxymethyl chloride (5.18 g) in dry acetonitrile (15 ml). The reaction mixture was stirred overnight at room temperature. The precipitate was removed by filtration and the filtrated evaporated under reduced pressure at 35° C. to give 2-(2-benzoyloxyethoxy)ethoxymethyl acetate (5.5 g) as a pale yellow oil. NMR and IR spectra were consistent with this structure.

A mixture of guanine diacetate (1.31 g), 2-(2-benzoyloxyethoxy)ethoxymethyl acetate (2.37 g), p-toluenesulfonic acid (32 mg) and mineral oil (5.2 g) was heated at 120° C. with stirring for 18 hours. The reaction mixture was cooled and the mineral oil decanted off. The residue was triturated with benzene and the benzene decanted off. To the residue was added 40% aqueous methylamine (10 ml), and the mixture was heated in a steam bath for 30 minutes. The water and methylamine were removed under reduced pressure and the residue extracted with hot ethanol. The ethanol-insoluble material was dissolved in boiling methanol, filtered, concentrated to 125 ml and cooled to room temperature, precipitating an impure product (166 mg) which was unmoved by filtration. The filtrate was chilled and 9-[2-(2-hydroxyethoxy)ethoxymethyl]guanine (80 mg, m.p. 184°–187° C.) was obtained.

EXAMPLE 4

| Oil in Water Cream base | |
|---|---|
| 9-[2-(2-Hydroxyethoxy)ethoxymethyl]guanine | 5.0 g |
| Lanolin, Anhydrous | 20.0 g |
| Polysorbate 60 | 4.0 g |
| Sorbitan Monopalmitate | 2.0 g |
| Light Liquid Paraffin | 4.0 g |
| Propylene Glycol | 5.0 g |
| Methyl Hydroxybenzoate | 0.1 g |
| Purified Water | to 100.0 g |

EXAMPLE 5

| Water Soluble Ointment Base | |
|---|---|
| 9-[2-(2-Hydroxyethoxy)ethoxymethyl]guanine | 0.5 g |
| Glycerol | 15.0 g |
| Macrogol 300 | 20.0 g |
| Polyethylene Glycol 1500 | 64.5 g |

EXAMPLE 6

| Tablet - (Total weight 359 mg) | |
|---|---|
| 9-[2-(2-Hydroxyethoxy)ethoxymethyl]guanine | 100 mg |
| Lactose | 200 mg |
| Starch | 50 mg |
| Polyvinylpyrrolidone | 5 mg |
| Magnesium Stearate | 4 mg |

EXAMPLE 7

| Tablet - (Total weight 359mg) | |
|---|---|
| 2-Amino-6-chloro-9-[2-(2-benzoyloxyethoxy)ethoxymethyl]purine | 100 mg |
| Lactose | 200 mg |
| Starch | 50 mg |
| Polyvinylpyrrolidone | 5 mg |
| Magnesium stearate | 4 mg |

EXAMPLE 8

| Tablet - (Total weight 359mg) | |
|---|---|
| 2,6-Diamino-9-[2-(2-hydroxyethoxy)ethoxymethyl]purine | 100 mg |
| Lactose | 200 mg |
| Starch | 50 mg |
| Polyvinylpyrrolidone | 5 mg |
| Magnesium stearate | 4 mg |

What is claimed is:

1. A compound of the formula I

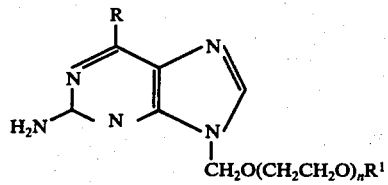

where
$n$ is an integer of 2 to 10
R is halogen, hydroxy or amino
$R^1$ is hydrogen or

where $R^2$ is hydrogen, alkyl of 1 to 8 carbons, phenyl or naphthyl or a pharmaceutically acceptable salt thereof.

2. The compound or salt of claim 1 in which R is chlorine.
3. The compound or salt of claim 1 in which $n$ is 2 to 4.
4. The compound or salt of claim 1 in which $n$ is 2.
5. The compound or salt of claim 1 in which R is amino.
6. The compound or salt of claim 1 in which R is OH.
7. The compound or salt of claim 1 in which $R^1$ is

8. 2-amino-6-chloro-9-[2-(2-benzoyloxyethoxy)ethoxymethyl] purine.

9. 2,6-Diamino-9-[2-(2-hydroxyethoxy)ethoxymethyl] purine.
10. 9-[2-hydroxyethoxy)ethoxymethyl] guanine.
11. The compound or salt of claim 1 in which $R^2$ is alkyl of 1 to 4 carbons.
12. The compound or salt of claim 1 in which $R^2$ is phenyl.
13. The compound or salt of claim 1 in which $R^2$ is napthyl.
14. The compound or salt of claim 1 in which $R^2$ is hydrogen.
15. The compound of claim 2 where $n$ is 2 to 4.
16. The compound of claim 15 in which $n$ is 2.
17. The compound or salt of claim 14 in which $n$ is 2.
18. A pharmaceutical composition comprising an effective non-toxic antiviral amount of a compound of the formula I

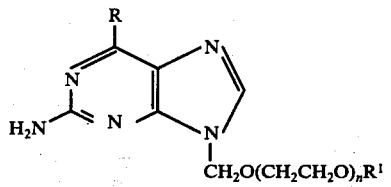

where
$n$ is an integer of 2 to 10
R is halogen, hydroxy or amino
$R^1$ is hydrogen or

where $R^2$ is hydrogen, alkyl of 1 to 8 carbons, phenyl or naphthyl or a pharmaceutically acceptable salt thereof in association with a pharmaceutically acceptable carrier therefore.

19. The composition of claim 18 in which R is chlorine.
20. The composition of claim 18 in which $n$ is 2 to 4.
21. The composition of claim 18 in which $n$ is 2.
22. The composition of claim 18 in which R is amino.
23. The composition of claim 18 in which R is OH.
24. The composition of claim 18 in which $R^1$ is

25. The composition of claim 18 in which the composition comprises 2-amino-6-chloro-9-purine or a pharamaceutically acceptable salt thereof.
26. The composition of claim 18 in which the composition comprises 2,6-Diamino-9-purine or a pharmaceutically acceptable salt thereof.
27. The composition of claim 18 in which the composition comprises 9-guanine or a pharmaceutically acceptable salt thereof.
28. The composition of claim 18 in which $R^2$ is alkyl of 1 to 4 carbons.
29. The composition of claim 18 in which $R^2$ is phenyl.
30. The composition of claim 18 in which $R^2$ is napthyl.
31. The composition of claim 18 in which $R^2$ is hydrogen.

32. The composition of claim 19 where n is 2 to 4.
33. The composition of claim 19 in which n is 2.
34. The composition of claim 22 in which n is 2 to 4.
35. The method of treating a susceptible virus infection of mammal which comprises administering to said virus infected mammal an effective non toxic antiviral treatment amount of a compound of the formula I $$\text{(I)}$$

[Structure: purine-like ring system with R at top, $H_2N$ attached, and $CH_2O(CH_2CH_2O)_nR^1$ substituent]

where
n is an integer of 2 to 10
R is halogen, hydroxy or amino
$R^1$ is hydrogen or $$\overset{O}{\underset{}{\|}}CR^2$$

where
$R^2$ is hydrogen, alkyl of 1 to 8
carbons, phenal naphthyl or a pharmaceutically acceptable salt thereof.
36. The method of claim 35 in which R is chlorine.
37. The method of claim 35 in which n is 2 to 4.
38. The method of claim 35 in which n is 2.
39. The method of claim 35 in which R is $NH_2$.
40. The method of claim 35 in which R is OH.
41. The method of claim 35 in which $R^1$ is $$\overset{O}{\underset{}{\|}}CR^2.$$

42. The method of claim 35 in which 2-amino-6-chloro-9-purine or a pharmaceutically acceptable salt thereof is administered.
43. The method of claim 35 in which 2,6-Diamino-9-purine or a pharmaceutically acceptable salt thereof is administered.
44. The method of claim 35 in which 9-guanine or a pharmaceutically acceptable salt thereof is adminstered.
45. The method of claim 35 in which $R^2$ is alkyl of 1 to 4 carbons.
46. The method of claim 35 in which $R^2$ is phenyl.
47. The method of claim 35 in which $R^2$ is napthyl.
48. The method of claim 35 in which $R^2$ is hydrogen.
49. The method of claim 36, where n is 2 to 4.
50. The method of claim 36 in which n is 2.
51. The method of claim 35 in which the virus is herpes.
52. The method of claim 51 in which the virus is herpes simplex.
53. The method of claim 35 in which the compound is administered orally or parenterally.
54. The method of claim 35 in which the amount is 0.1 to 250 mg/kg of mammal bodyweight.
55. The compound or salt of claim 5 where n is 2 to 4.
56. The compound or salt of claim 6 where n is 2 to 4.
57. The compound or salt of claim 11 where n is 2 to 4.
58. The compound or salt of claim 12 where n is 2 to 4.
59. The compound or salt of claim 13 where n is 2 to 4.
60. The compound or salt of claim 14 where n is 2 to 4.
61. The compound or salt of claim 5 in which n is 2.
62. The compound or salt of claim 6 in which n is 2.
63. The compound or salt of claim 11 in which n is 2.
64. The compound or salt of claim 12 in which n is 2.
65. The compound or salt of claim 13 in which n is 2.
66. A pharmaceutically acceptable salt of 2-amino-6-chloro-9-[2-(2-benzoyloxyethoxy)-ethoxymethyl]purine.
67. A pharmaceutically acceptable salt of 2,6-Diamino9-[2-(2-hydroxyethoxy)ethoxymethyl]purine.
68. A pharmaceutically acceptable salt of 9-[2-(2-hydroxyethoxy)ethoxymethyl]guanine.
69. The composition of claim 23 in which n is 2 to 4.
70. The composition of claim 28 in which n is 2 to 4.
71. The composition of claim 29 in which n is 2 to 4.
72. The composition of claim 30 in which n is 2 to 4.
73. The composition of claim 31 in which n is 2 to 4.
74. The composition of claim 22 in which n is 2.
75. The composition of claim 23 in which n is 2.
76. The composition of claim 28 in which n is 2.
77. The composition of claim 29 in which n is 2.
78. The composition of claim 30 in which n is 2.
79. The composition of claim 31 in which n is 2.
80. The method of claim 40 in which n is 2 to 4.
81. The method of claim 45 in which n is 2 to 4.
82. The method of claim 46 in which n is 2 to 4.
83. The method of claim 47 in which n is 2 to 4.
84. The method of claim 48 in which n is 2 to 4.
85. The method of claim 42 in which the virus is herpes simplex or zoster and the amount is 0.1 to 250 mg/kg of mammal bodyweight.
86. The method of claim 43 in which the virus is herpes simplex or zoster and the amount is 0.1 to 250 mg/kg of mammal bodyweight.
87. The method of claim 44 in which the virus is herpes simplex or zoster and the amount is 0.1 to 250 of mammal bodyweight.

* * * * *